United States Patent
Wen et al.

(10) Patent No.: US 6,923,188 B2
(45) Date of Patent: Aug. 2, 2005

(54) METHOD OF SAMPLING CONTAMINANTS OF SEMICONDUCTOR WAFER CARRIER

(75) Inventors: Rui-Hui Wen, Hsin-Chu Hsien (TW); Huei-Ming Ting, Hsin-Chu Hsien (TW)

(73) Assignee: Powerchip Semiconductor Corp., Hsin-Chu (TW)

( * ) Notice: Subject to any disclaimer, the term of this patent is extended or adjusted under 35 U.S.C. 154(b) by 14 days.

(21) Appl. No.: 10/249,672

(22) Filed: Apr. 29, 2003

(65) Prior Publication Data

US 2004/0216766 A1 Nov. 4, 2004

(51) Int. Cl.$^7$ ................................................ B08B 9/093
(52) U.S. Cl. ................ 134/22.18; 134/21.1; 134/24; 134/34; 134/42; 134/902; 73/863; 73/863.71; 73/864; 73/864.33
(58) Field of Search ................ 134/22.1, 22.18, 134/24, 34, 42, 902, 18; 73/863, 863.71, 864, 864.33, 53.01, 64, 646, 61.41, 64.56

(56) References Cited

U.S. PATENT DOCUMENTS

| | | | | |
|---|---|---|---|---|
| 5,660,585 A | * | 8/1997 | Swoboda et al. | 454/187 |
| 5,711,821 A | * | 1/1998 | Turner et al. | 134/21 |
| 5,752,985 A | * | 5/1998 | Nagafune et al. | 29/25.01 |
| 6,248,177 B1 | * | 6/2001 | Halbmaier | 134/2 |
| 6,432,214 B2 | * | 8/2002 | Bryer et al. | 134/10 |
| 6,676,770 B2 | * | 1/2004 | Hou et al. | 134/34 |
| 2002/0100495 A1 | * | 8/2002 | Bexten et al. | 134/18 |

* cited by examiner

*Primary Examiner*—M. Kornakov
(74) *Attorney, Agent, or Firm*—Winston Hsu

(57) ABSTRACT

A method of sampling contaminants of a semiconductor wafer carrier. The method includes placing a tool chamber in a clean room and then placing and fixing the semiconductor wafer carrier with its opening facing downward inside the tool chamber. Then the method includes using at least one nozzle to spray extraction fluid uniformly on the inner surfaces of the semiconductor wafer carrier and collecting the extraction fluid.

19 Claims, 3 Drawing Sheets

METHOD OF SAMPLING CONTAMINANTS OF SEMICONDUCTOR WAFER CARRIER

BACKGROUND OF INVENTION

1. Field of the Invention

The present invention relates to a method of sampling contaminants of a semiconductor wafer carrier, and more particularly to a method of sampling contaminants of a front opening unified pod (FOUP).

2. Description of the Prior Art

The diameter of semiconductor wafer is changing from eight inches to twelve inches because of the progress of the semiconductor industry and the consideration of economic effects. For conveying semiconductor wafers in an effort-saving, safe, and clean way, a front opening unified pod (FOUP) is used as a wafer carrier in the present foundry. The FOUP that is manipulateable and exchangeable is also used to store wafers temporarily for reducing the required area of clean room.

Referring to FIG. 1, it is a schematic diagram of a semiconductor wafer carrier 10. As shown in FIG. 1, the wafer carrier 10 is able to load twenty-five wafers, and a plurality of breathing filters 14 are positioned on the sidewalls of the wafer carrier 10. The main function of the wafer carrier 10 is conveying the wafers 12 to equipment during different processes. Since the wafers 12 have to be treated by 300 to 600 processes, the inner surfaces of the wafer carrier 10 may be polluted. Furthermore, the contaminants of the wafer carrier 10 may pollute the loaded wafers 12, which results in self-contamination. Therefore, it is necessary to sample and analyze the contaminants of the wafer carrier 10 so as to control and realize the relationship between contamination and production yield.

The prior art method of sampling contaminants of the wafer carrier 10 includes directly pouring deionized water into the wafer carrier 10. After twenty-four hours, the deionized water is drawn from the wafer carrier 10 for performing contamination analysis. However, the prior art method does not define a complete set of sampling procedure and environment, which critically affects the accuracy and certainty of sampling results.

SUMMARY OF INVENTION

It is therefore an object of the claimed invention to provide a method of sampling contaminants of a semiconductor wafer carrier so as to solve the above-mentioned problems.

According to the claimed invention method of sampling contaminants of a semiconductor wafer carrier, the method includes placing a tool chamber in a clean room and then placing and fixing the semiconductor wafer carrier with its opening facing downward inside the tool chamber. Then the method includes using at least one nozzle to spray extraction fluid uniformly on the inner surfaces of the semiconductor wafer carrier and collecting the extraction fluid.

The claimed invention method of sampling contaminants of a semiconductor wafer carrier includes first providing a clean room including a chemical composition filter and a particle filter, and then placing a clean and dry tool chamber in the clean room. Finally, the semiconductor wafer carrier is placed and fixed in the tool chamber, and a nozzle is used to uniformly spray extraction fluid on the inner surfaces of the semiconductor wafer carrier for sampling contaminants. Comparing to the prior art method, the claimed invention method includes a complete set of sampling procedure and environment, which substantially improves the accuracy and certainty of sampling results.

These and other objects of the present invention will be apparent to those of ordinary skill in the art after reading the following detailed description of the preferred embodiments, which are illustrated in the multiple figures and drawings.

DETAILED DESCRIPTION

Figure 1:
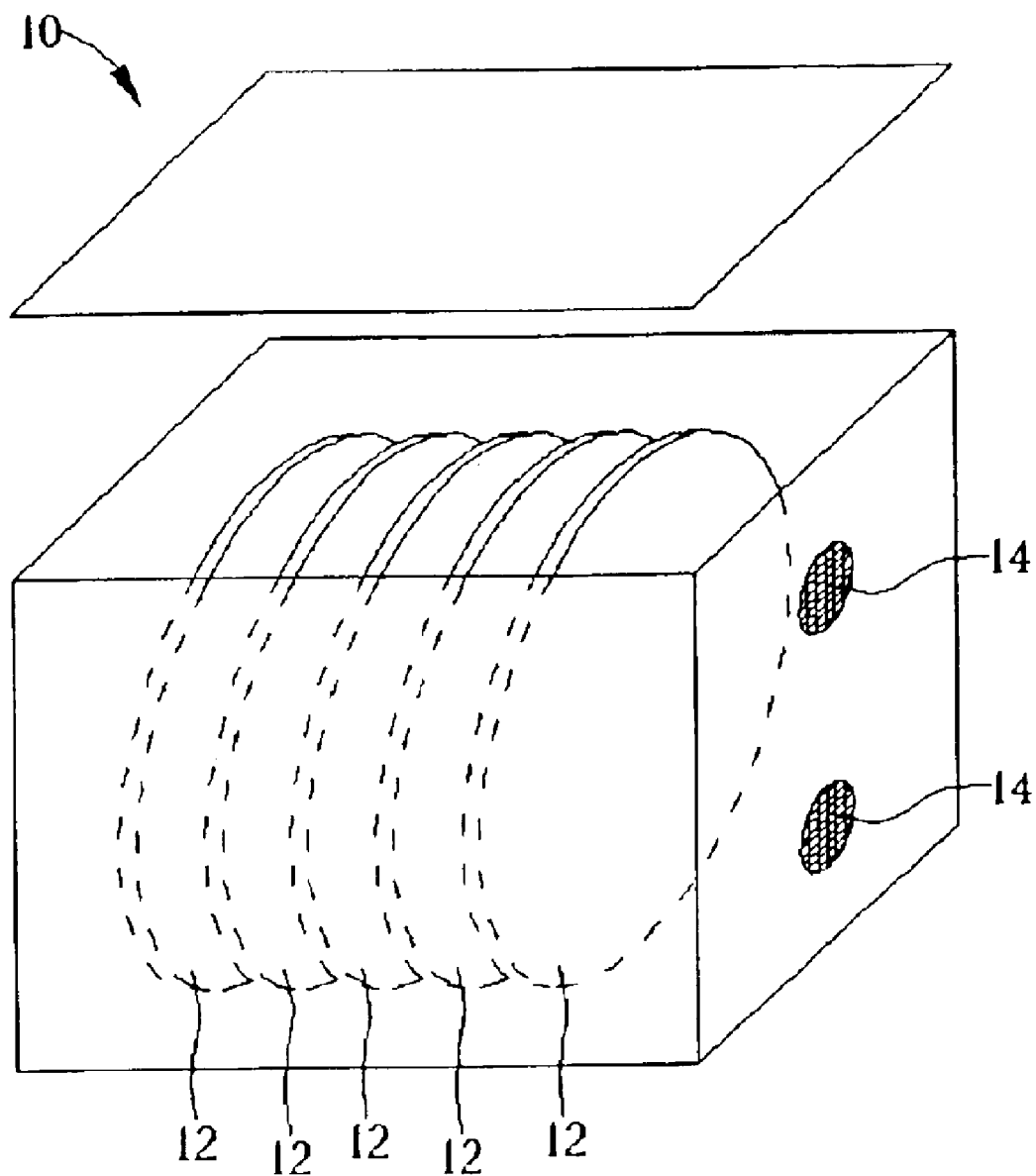
FIG. 1 is a schematic diagram of a prior art semiconductor wafer carrier.
Figure 2:
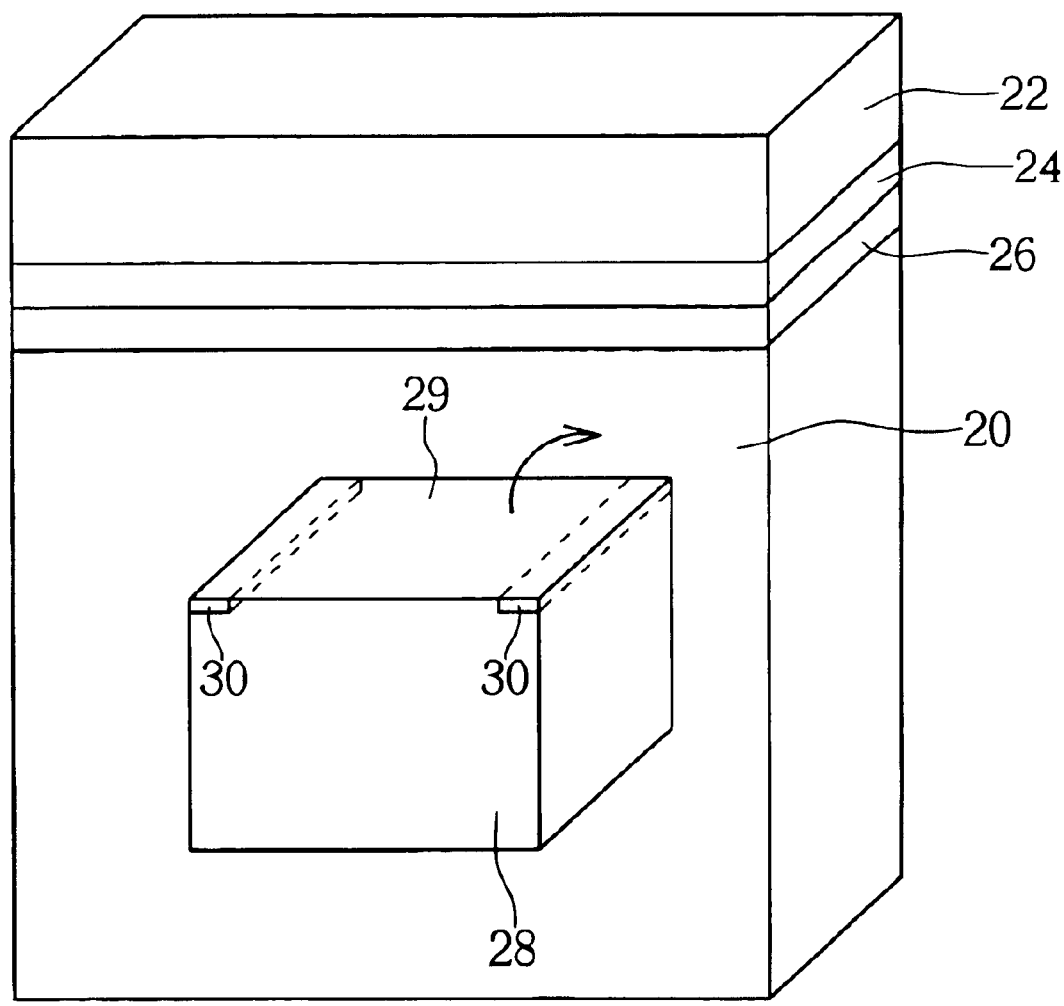
FIG. 2 and FIG. 3 are schematic diagrams of the present invention method of sampling contaminants of a semiconductor wafer carrier.

The present invention provides a method of sampling contaminants of a semiconductor wafer carrier. As shown in FIG. 2, the method includes providing a clean room 20 with a fan 22, a chemical composition filter 24 for filtrating oxynitride and oxysulfide, and a boron free ultra low penetration air (ULPA) filter 26 for filtrating particles. A tool chamber 28, having a top opening 29, is then placed in the clean room 20, and a stopper 30 of one-centimeter width is positioned on the inner edge of the top opening 29 of the tool chamber 28, which is used for preventing the air within the clean room 20 from flowing into the tool chamber 28.

Figure 3:
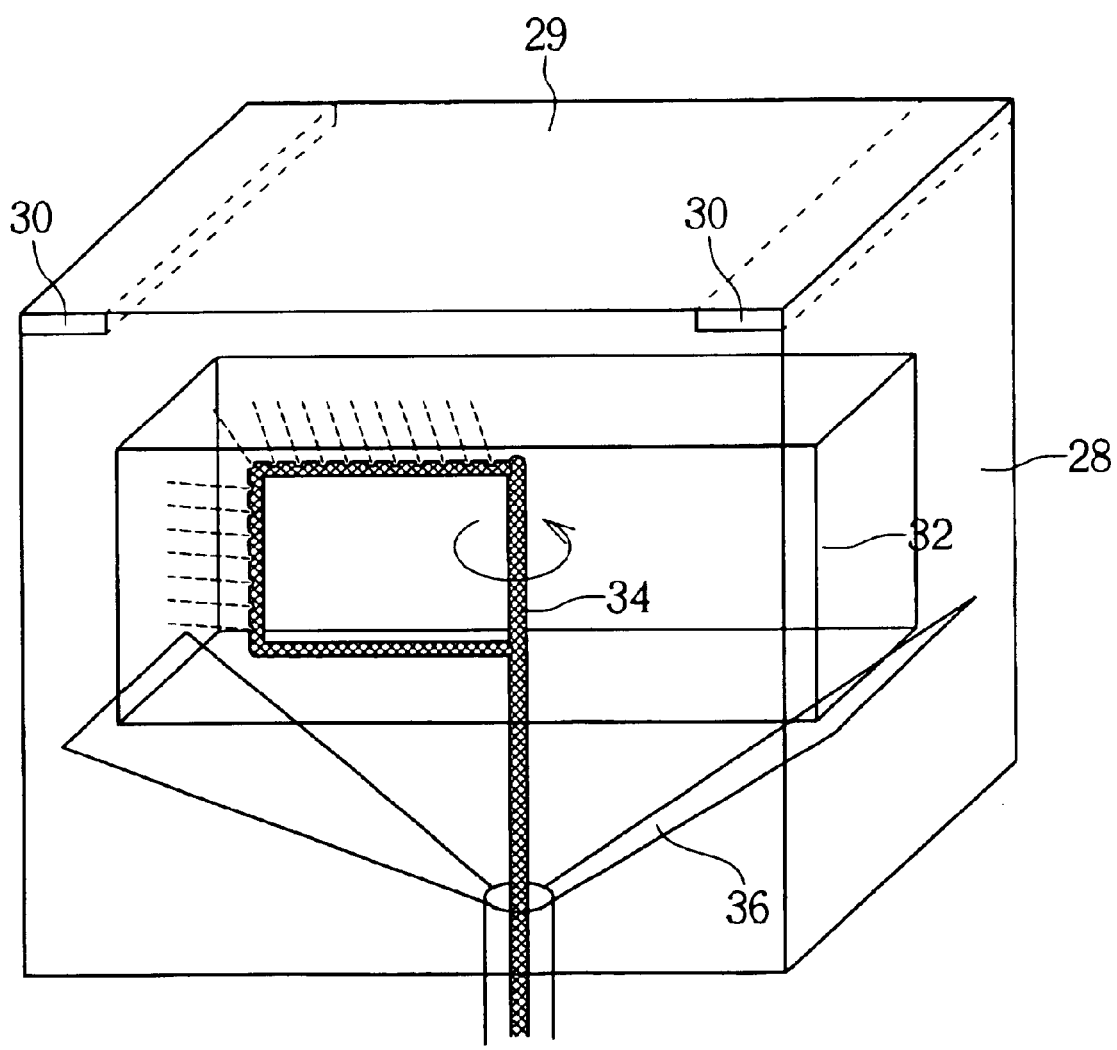

Then as shown in FIG. 3, a semiconductor wafer carrier, such as a front opening unified pod (FOUP) 32, is placed inside the tool chamber 28, and an opening of the FOUP 32 is facing downward. Four pillars (not shown in FIG. 3) installed in the tool chamber 28 are used to fix the position of the FOUP 32. Finally, a loop type nozzle 34 is used to spray extraction fluid uniformly on the inner surfaces of the FOUP 32. An inclined plane 36 formed in the bottom of the tool chamber 28 is positioned under the opening of the FOUP 32 for collecting the extraction fluid, which is then treated by qualitative and quantitative analysis of organic matters, inorganic matters and trace metals. It should be appreciated that the method of the present invention is not limited to analyzing the FOUP 32, and can be used to analyze other semiconductor wafer carriers, such as the standard mechanical interface pod (SMIF).

For spraying the extraction fluid uniformly on the inner surfaces of the FOUP 32, the loop type nozzle 34 is able to rotate within 360 degrees, and each outlet of the nozzle 34 has uniform pressure. The present invention method also includes controlling the rotation rate of the nozzle 34 for increasing a covering area of the extraction fluid. The extraction fluid includes deionized water and helium (He), argon (Ar) such clean gas that is used as carrier gas. The present invention method includes controlling the quantity of deionized water and carrier gas so as to form a column of the extraction fluid or a mist of the extraction fluid. Furthermore, the present invention method includes controlling temperature of the extraction fluid so as to improve sampling efficiency.

Before placing the FOUP 32 inside the tool chamber 28 for sampling contaminants, the present invention method includes cleaning and drying the tool chamber 28 so as to prevent the sampling results from being influenced. When cleaning the tool chamber 28, the nozzle 34 is used to spray deionized water and hydrogen peroxide solution uniformly inside the tool chamber 28. And when drying the tool chamber 28, the nozzle 34 is used to spray dry gas uniformly inside the tool chamber 28.

In summary, the present invention method of sampling contaminants of a semiconductor wafer carrier includes the following steps:

1. providing a clean room;
2. placing a tool chamber in the clean room;
3. cleaning the tool chamber;
4. drying the tool chamber;
5. placing and fixing a FOUP inside the tool chamber;
6. setting the rotation rate of the nozzle and setting the temperature and type (column or mist) of the extraction fluid;
7. using the nozzle to spray the extraction fluid uniformly on the inner surfaces of the FOUP for a predetermined duration; and
8. collecting the extraction fluid so as to perform contamination analysis.

The present invention method of sampling contaminants of a semiconductor wafer carrier includes first providing a clean room including a chemical composition filter and a particle filter, and then placing a clean and dry tool chamber in the clean room. Finally, the semiconductor wafer carrier is placed and fixed in the tool chamber, and a nozzle is used to uniformly spray extraction fluid on the inner surfaces of the semiconductor wafer carrier for sampling contaminants. Comparing to the prior art method, the present invention method includes a complete set of sampling procedure and environment, which substantially improves the accuracy and certainty of sampling results.

Those skilled in the art will readily observe that numerous modifications and alterations of the device may be made while retaining the teaching of the invention. Accordingly, the above disclosure should be construed as limited only by the metes and bounds of the appended claims.

What is claimed is:

1. A method of sampling contaminants of a semiconductor wafer carrier comprising:
   placing a tool chamber in a clean room;
   placing and fixing a semiconductor wafer carrier with its opening facing downward inside the tool chamber;
   using at least one nozzle to spray extraction fluid uniformly on the inner surfaces of the semiconductor wafer carrier, wherein the extraction fluid comprises deionized water and carrier gas; and
   collecting the extraction fluid.

2. The method of sampling contaminants of claim 1, wherein the clean room comprises a chemical composition filter and a particle filter.

3. The method of sampling contaminants of claim 2, wherein the chemical composition filter is used for filtering oxynitride and oxysulfide.

4. The method of sampling contaminants of claim 1, wherein a stopper is positioned on the inner edge of an opening of the tool chamber and is used for preventing the air within the clean room from flowing into the tool chamber.

5. The method of sampling contaminants of claim 1, wherein the nozzle is a loop type nozzle.

6. The method of sampling contaminants of claim 1 further comprising controlling the quantity of deionized water and carrier gas so as to form a column of the extraction fluid or a mist of the extraction fluid.

7. The method of sampling contaminants of claim 1 further comprising controlling temperature of the extraction fluid so as to improve sampling efficiency.

8. The method of sampling contaminants of claim 1, wherein the semiconductor wafer carrier comprises a front opening unified pod (FOUP) and a SMIF pod.

9. The method of sampling contaminants of claim 1 further comprising cleaning and drying the tool chamber before sampling contaminants of the semiconductor wafer carrier.

10. The method of sampling contaminants of claim 9 further comprising using the nozzle to spray deionized water and hydrogen peroxide solution uniformly inside the tool chamber for cleaning the tool chamber.

11. The method of sampling contaminants of claim 9 further comprising using the nozzle to spray dry gas uniformly inside the tool chamber for drying the tool chamber.

12. A method of sampling contaminants of a semiconductor wafer carrier comprising:
    placing a tool chamber in a clean room;
    cleaning the tool chamber by using at least one nozzle to spray deionized water and hydrogen peroxide solution uniformly inside the tool chamber;
    drying the tool chamber;
    placing and fixing a semiconductor wafer carrier with its opening facing downward inside the tool chamber;
    using the nozzle to spray extraction fluid uniformly on the inner surfaces of the semiconductor wafer carrier; and
    collecting the extraction fluid.

13. The method of sampling contaminants of claim 12, wherein the clean room comprises a chemical composition filter and a particle filter.

14. The method of sampling contaminants of claim 13, wherein the chemical composition filter is used for filtering oxynitride and oxysulfide.

15. The method of sampling contaminants of claim 12, wherein a stopper is positioned on the inner edge of an opening of the tool chamber and is used for preventing the air within the clean room from flowing into the tool chamber.

16. The method of sampling contaminants of claim 12, wherein the nozzle is a loop type nozzle.

17. The method of sampling contaminants of claim 12, further comprising controlling temperature of the extraction fluid so as to improve sampling efficiency.

18. The method of sampling contaminants of claim 12, wherein the semiconductor wafer carrier comprises a front opening unified pod (FOUP) and a SMIF pod.

19. The method of sampling contaminants of claim 12 further comprising using the nozzle to spray dry gas uniformly inside the tool chamber for drying the tool chamber.

* * * * *